United States Patent [19]

Behringer

[11] Patent Number: 4,514,172
[45] Date of Patent: Apr. 30, 1985

[54] APPARATUS SUPPORTING A PLURALITY OF DENTAL INSTRUMENTS

[75] Inventor: Wolfgang Behringer, Bensheim, Fed. Rep. of Germany

[73] Assignee: Siemens Aktiengesellschaft, Berlin & Munich, Fed. Rep. of Germany

[21] Appl. No.: 552,779

[22] Filed: Nov. 17, 1983

[30] Foreign Application Priority Data

Nov. 23, 1982 [DE] Fed. Rep. of Germany ....... 3243294

[51] Int. Cl.³ .............................................. A61C 1/08
[52] U.S. Cl. ................................................... 433/126
[58] Field of Search ................................ 433/126, 114

[56] References Cited

U.S. PATENT DOCUMENTS 4,217,101 8/1980 Logé .................................. 433/126

Primary Examiner—Robert Peshock
Attorney, Agent, or Firm—Hill, Van Santen, Steadman & Simpson

[57] ABSTRACT

An apparatus, which supports dental handpieces and supplies necessary operating agents to the handpiece, which has a hose containing supply lines extending to a connecting member, includes a housing having a support recess for each handpiece, a coupling member for each support recess to coact with the connecting member of the handpiece to connect agent lines in the housing to the supply line, and a control arrangement which selectively controls the flow of agents to the elements of the coupling member including an evaluation arrangement which receives signals indicating the type of handpiece being connected to the coupling member and selectively connecting the various sources to the elements or the coupling member in response to the indicated handpiece. The coupling and connecting members have cooperating coding pins and sockets for creating a signal to indicate the type of handpiece being connected by the coupling member so that the evaluation arrangement automatically selects the desired agents for a specific type of handpiece when the handpiece is connected to the coupling member. With this arrangement, each of the coupling members can receive the connecting members from a large variety of dental handpieces and thus the user can selectively connect any dental handpiece to a particular position.

6 Claims, 5 Drawing Figures

APPARATUS SUPPORTING A PLURALITY OF DENTAL INSTRUMENTS

BACKGROUND OF THE INVENTION

The present invention is directed to an apparatus for supporting a handpiece and for supplying necessary operating agents to the handpiece, which will have a hose with supply lines extending to a connecting member. The apparatus includes a housing having a support arrangement including at least one support recess for receiving and storing each dental handpiece, a coupling member for each support recess coacting with the connecting member of the handpiece to connect agent lines in the housing to the supply lines of the hose of the handpiece. The apparatus also includes a control arrangement for selectively controlling the particular agents required for that handpiece.

It is known to provide an apparatus which provides each dental instrument or handpiece with an associate module to control the flow or supply of agents to the instrument and to support the handpiece. The supply lines for the particular handpiece are firmly connected to the associated module. For example, the handpiece will have a supply hose with a connecting element or member which has standard connecting fittings that are connected to standard connecting fittings on the module. The disposition and sequence of the instrument holders is first prescribed. Given a desire for an additional instrument or for a different placement of the instruments in the arrangement, the purchaser or user must carry out a modification of the instrument holders of the apparatus. When, for example, a given instrument complement of one electrical motor handpiece and two turbine handpieces is provided and there is a desire to either add a second electrical handpiece or to add a surgical instrument, the arrangement of the modules must be changed with a removal of the module corresponding to the undesired instrument and its replacement by a module for the desired instrument. A rearrangement of the instruments in the framework of the daily operation routine in order, for example, to have an instrument at a different location in the support holder for grasping oriented reasons is only possible with the rearrangement of the modules in the system or apparatus.

SUMMARY OF THE INVENTION

The present invention is directed to providing an apparatus for supporting dental handpieces and supplying necessary operating agents to the handpieces, which apparatus enables the purchaser to arrange the dental handpieces in any particular order and sequence and enables changing the order or sequence as desired with either the addition, deletion or replacement of various handpiece instruments.

In order to accomplish these goals, the present invention is directed to an improvement for an apparatus for supporting a handpiece and for supplying necessary operating agents to the handpiece, said handpiece having a hose containing supply lines extending to a connecting member, the apparatus including a housing having support means including at least one support recess for receiving and storing each dental handpiece, a coupling member for each support recess coacting with the connecting member of a handpiece to connect the agent supply lines in the housing to the supply lines of the hose of the dental handpiece, and control means for selectively controlling the flow of the agents to the handpiece. The improvements include the housing having a source of water, a source of air and at least one source of electrical power, each coupling member being disposed on an easily accessible portion of the housing, each coupling member and coacting connecting member being designed for easy releasable interconnection, said coupling member being constructed with elements for separately transferring electrical power, air and water from the sources in the housing to the connecting member of the handpiece, said control means including evaluation means for receiving signals indicating the type of handpiece being connected to the coupling member and for selectively connecting the various sources to the elements of the coupling member in response to the indicated type of handpiece, and said coupling member and connecting member having coacting coding means for creating a signal to indicate the type of handpiece so that the particular sources required for the handpiece are separately connected to the supply lines of the hose of the handpiece when the connecting member and coupling member are interconnected.

Preferably, the apparatus will have a plurality of coupling members and will have an electrical source for an electrical motor-driven handpiece, plus an electrical source for an ultrasonically-driven handpiece and fluid sources such as air pressure for a turbine-driven handpiece. In addition, the apparatus may have a high frequency power source for a high frequency surgical handpiece. With each of these power sources, connected to each of the coupling members, any of the handpieces, whether it is an electrically-driven motor handpiece, an ultrasonic-driven handpiece, a turbine-driven handpiece or a high frequency surgical instrument can be connected to the particular coupling member and is interchangeable at that position. With this interchangeability, the customer can determine the particular sequence and position for the handpieces that are being used. If a change in the sequence and position is desired, it can be easily accomplished. In addition, a handpiece can be easily replaced if necessary, for example, due to clogged lines, wear or requirement of sterilization of the entire handpiece and hose. As mentioned, with the provision of a power source for a high frequency surgical instrument, this instrument which is rarely used in comparison with electrical motor-driven handpieces and turbine handpieces can be inserted into the arrangement of dental handpieces when necessary. In addition, it can be placed at any position so that it can be easily grasped by the physician when being used.

A significant advantage of the present invention is that it provides an apparatus, which has a control device that enables the purchaser to change instruments at any time and arrange them in any arbitrary sequence which he or she has selected. Moreover, the purchaser can connect a multitude of additional instruments that are identical or differently designed to the usual standard supply system, which can selectively supply an electrical motor, a turbine, an ultrasonic device and an HF surgical instrument. When, for example, four connecting fittings are provided on the apparatus, then either four handpieces with air and/or electro-mechanical drives can be provided in an identical or different structure regarding the drive, one or more ultrasonic or HF surgical handpieces can be provided or an arbitrary combination of the instruments in an arbitrary sequence can be provided. Subsequent rearrangements of the instruments only require a disconnecting and reconnection or plugging of the connecting members. The drive agents associated with the handpieces are then automatically preselected at the newly selected location due to the signal created by the coacting coding means on the coupling and connecting members and the evaluation means which evaluate this signal. The supplies belonging to the particular instruments thus need not be reequipped.

Plug-type members are advantageously provided as the coacting coupling and connecting members. The coding means comprises a plurality of coacting pins received in coacting sockets with bridge networks interconnecting selected pins for a particular instrument. Thus, if selected pins are interconnected, the evaluation means will receive a particular signal which is evaluated as belonging to a particular type of dental handpiece. The evaluation means accomplishes this detection by means of a logic operation to determine whether an instrument is connected and if so, what type of instrument is connected. After determining the particular type of instrument, it emits control signals for opening or selectively connecting the interconnection of the particular drive agents for that particular instrument.

DESCRIPTION OF THE PREFERRED EMBODIMENTS

Figure 1:
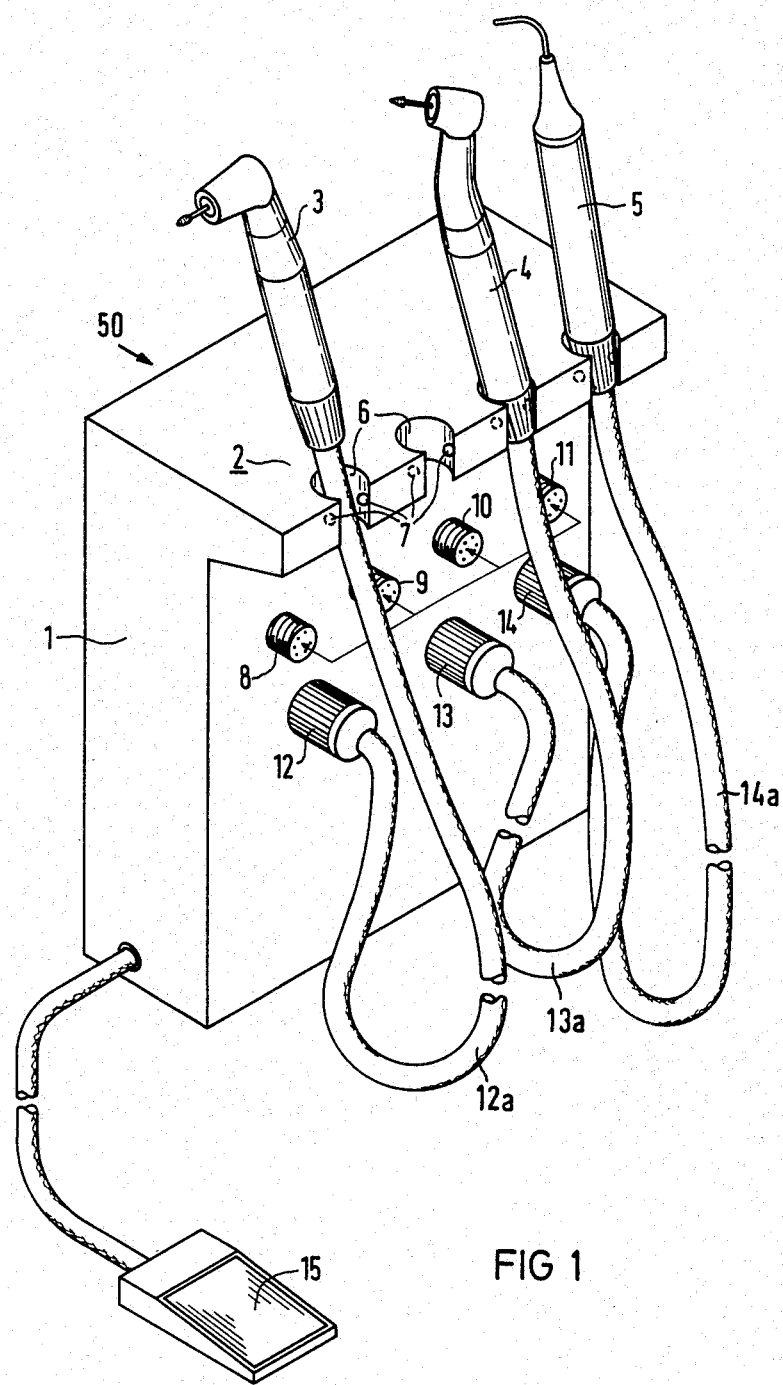
FIG. 1 is a perspective view of a dental device in accordance with the present invention.

The principles of the present invention are particularly useful when incorporated in an apparatus generally indicated at 50 in FIG. 1. The apparatus 50 has a housing 1 which on an upper end is provided with means for supporting and receiving dental instruments which is illustrated as a holder 2.

For the sake of clarity, only three instruments are illustrated. These consist of an electrically-driven motor handpiece 3, a pneumatically-driven or turbine-driven handpiece 4 and an ultrasonically-driven handpiece 5 which is used for removal of dental plaque. The holder 2 contains four annular deposit claws or recesses 6, which are open along one side so that when the instrument is lifted therefrom, the dental hose such as the hose 12a for the instrument 3 can be moved out of the recess or claw. In order to determine when each of the instruments are removed from its respective recess 6, a light barrier 7 is provided for each recess and consists of a transmitter and receiver which emits a switch pulse to the evaluation electronics which will be explained in greater detail hereinafter when the instrument or handpiece has been lifted from the recess and removed.

Figure 2:
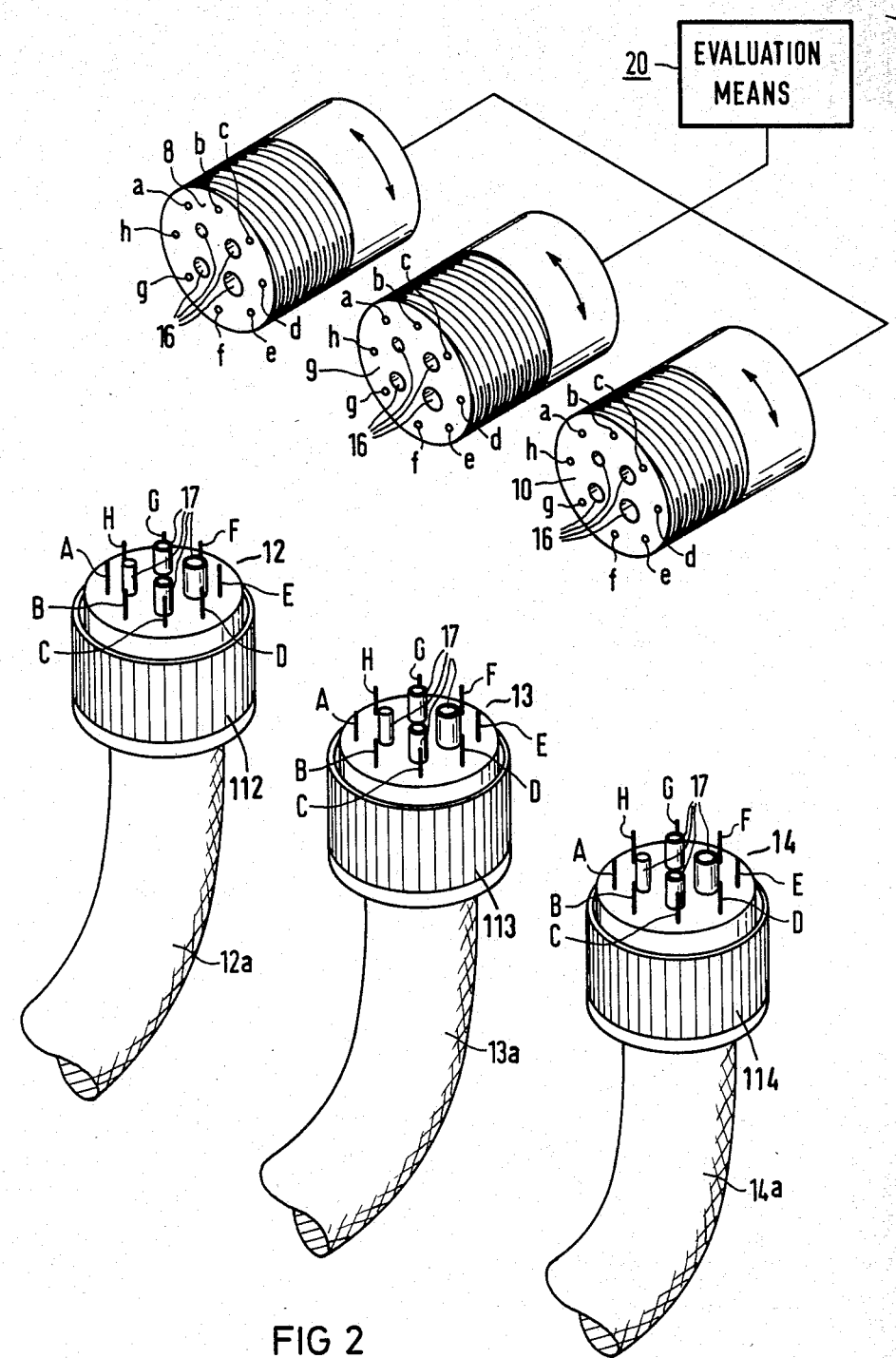
FIG. 2 is a perspective view of details of the coupling members and connecting members for forming the interconnection between the dental handpiece and the apparatus of the present invention.

In a convenient place on the housing 1, four coupling members 8-11 are provided with one coupling member for each of the recesses 6. Each of the handpieces such as the motor-driven handpiece 3 have a hose such as 12a terminating in a connecting member 12 while the member 4 has a connecting member 13 on a hose 13a and the handpiece 5 has a connecting member 14 on the end of a hose 14a. Each of the connecting members 12, 13 and 14 have means for forming a rapid-action coupling with the respective coupling member. As best illustrated in FIG. 2, this comprises a threaded sleeve 112, 113 or 114, which is threaded onto the respective coupling members such as 8-11. Preferably, in order to enable a uniform sag in each of the supply lines 12a-14a, the coupling members 8-11 are rotatably mounted on the surface of the housing 1 as diagrammatically illustrated in FIG. 2. It should be noted that under given conditions, they may be locked in a desired rotational position. At least the function of the on-off for the individual drives is controlled with a foot switch 15.

As best illustrated in FIG. 2, each of the coupling members 8-11 have four channels 16 in the center for forming the elements to transfer the operating agents such as spray air, drive air, return air and spray water. These four channels terminate in sockets and are arranged in a specific pattern which is the same for each of the coupling members such as disclosed by the arrangement in U.S. Pat. No. 4,080,737 which was based on German application No. 2,549,177. These operating agents are supplied to the channels 16 from supply sources through supply lines which are not illustrated. Each of the connecting members 12-14 have cooperating elements illustrated as plugs 17 which have the same spatial relationship as the channels 16. It is also noted that the size of the various channels are different and thus the connection of any one of the connecting members 12-14 and the coupling members 8-11 will always have the same orientation. It is also noted that as a result of this particular arrangement, any one of the connecting members 12-13 can be connected to any one of the coupling members 8-11.

When specific operating agents are not required for the particular instrument or handpiece, then the cooperating elements such as the projecting plug-shaped tubes 17 on the connecting member can either not be provided or are formed by a dummy pin or bushing. However, the coupling members 8-11 have all of the elements 16 for the operating agents. In addition, each of the coupling members include three electrical contact sockets f, g and h over which various voltage potentials for different types of electrical users can be transmitted. These contact sockets are part of a coding means which include coding sockets a, b, c, d and e. Thus, each of the coupling members 8-11 have eight sockets a-h which are arranged as illustrated in FIG. 2 concentrically around the center of the channels 16. The sockets a-h will receive coacting pins A-H which are on the connecting members 12-14. Of these connecting pins, A-E act as coding pin arrangements while the pins F, G and H are adapted to receive electrical outputs. Thus, the coding pins A-E will indicate whether a handpiece has been connected to given coupling members 8-11 and will also create a signal which will be received by an evaluation means 20 of a control means to specify which type of dental handpiece has been attached.

Figure 4A:
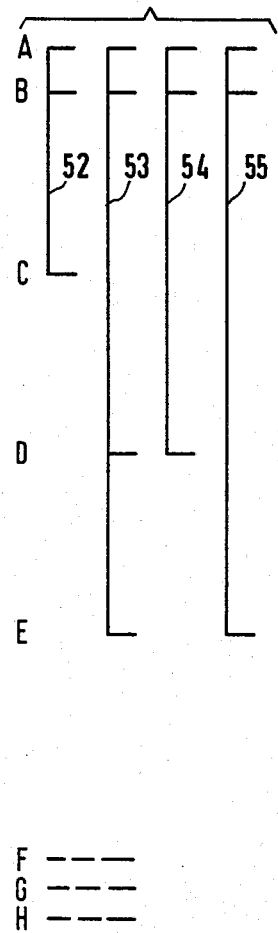
FIG. 4a is a diagrammatic view of the particular bridging arrangements for various dental handpieces.

The first five coding pins A-E are schematically indicated in FIG. 4a and are schematically illustrated as being interconnected in various combinations 52-55 by contact bridges to indicate a given type of dental handpiece. Each of these combinations 52-55 will provide a signal to the electronic circuit of the evaluation means 20 which is connected to each of the coupling members 8–11 to determine what type of dental handpiece is being connected. The contact pins F–H are connected to supply lines in the hoses of the respective handpiece and deliver the operating voltage for the particular handpiece in view of the particular evaluation of the type of handpiece being connected.

The light barrier 7 of each of the recesses or claws 6 of the handpiece support 2 are first switched on by the reception of the first contact pins A,B in the sockets a,b. When a connection of the pins A,B and the sockets a,b are formed, a supply for the light barrier which is referenced 19 in FIG. 4b receives a switched-on signal. The appertaining light barrier 7 is then switched on by a signal traveling on the control line 21 with a control line being associated with each of the individual recesses 6 of the support 2. The light barriers then provide information to the evaluation means 20 on a signal input line 22 as to whether the particular handpiece has been removed or is still deposited in the recess 6. This particular action will be described in greater detail with reference to a dental handpiece 3 which is an electrically-driven motor handpiece.

Figure 3:
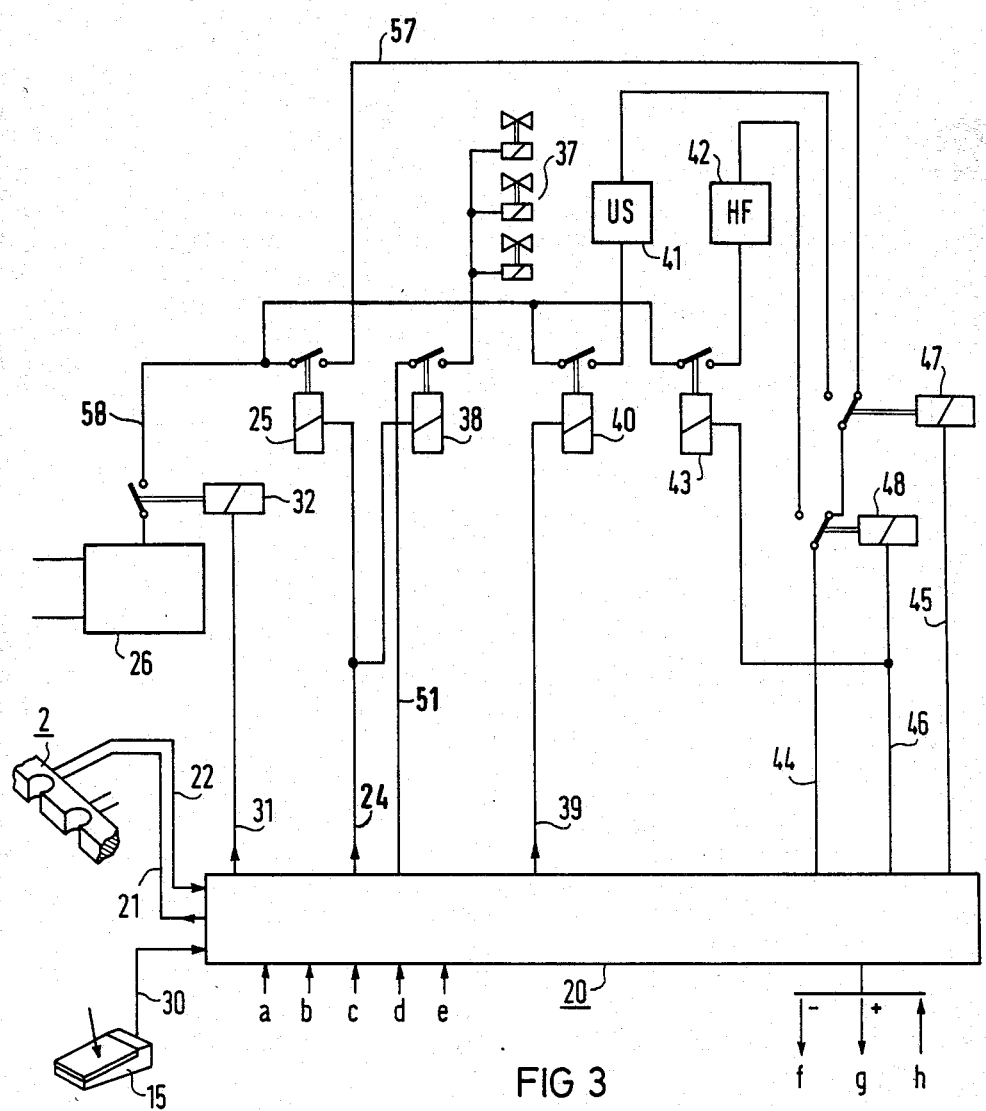
FIG. 3 is a fundamental circuit diagram of the control means.
Figure 4B:
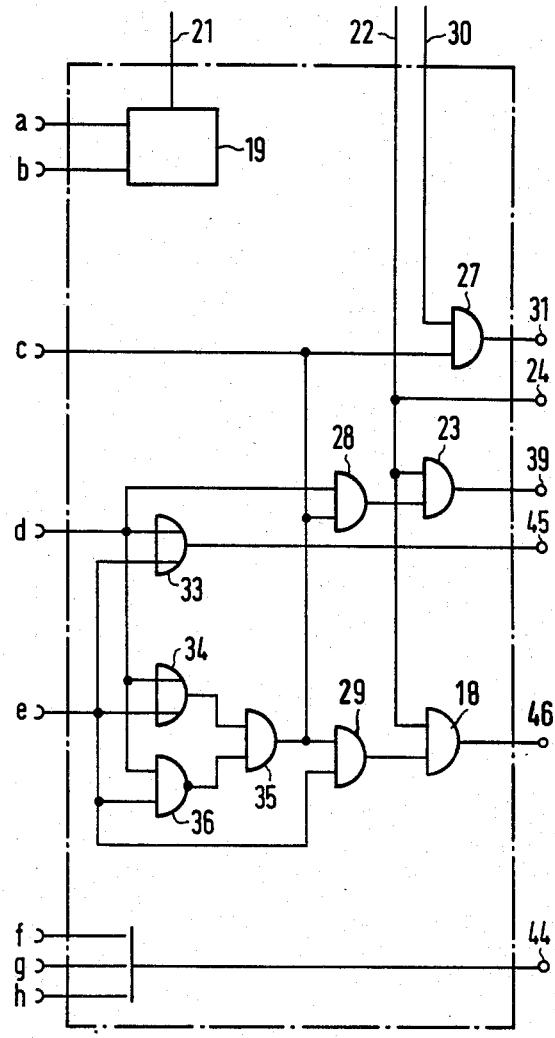
FIG. 4b is a detailed circuit diagram of the evaluation means of the control means of FIG. 3.

It is assumed that the handpiece 3 has been connected to the particular coupling member and is still deposited in the recess 6 of the support 2. Thus, the connecting member 12 is connected to the coupling member such as 8. Upon connecting, the evaluation means 20 first receives the information over the bridge contacts Aa/Bb and the control line 21 that a handpiece is connected with the consequence that the associated light barrier 7 is placed in operation, for example, is switched on. Upon removal of the handpiece from the support or holder, the evaluation means 20 will receive the light barrier signal on line 22 that the handpiece has been removed. This signal on the line 22 is applied to one input side of AND gates 18 and 23 and on the other hand is applied to a control line 24. The control line 24 actuates a relay 25 in a branch 57 of a power line 58 from a motor supply or control electronics 26 and also actuates a relay 38 in a line 51 from the evaluation means 20 that extend to a plurality of solenoid valves 37 which will be described hereinafter (see FIG. 3). With the combination 52 schematically illustrated in FIG. 4a, the bridge also includes the pin C which when received in the socket c as schematically illustrated in FIG. 4b, creates the signal which is applied to one side of an AND gate 27 and is also applied to one side of AND gates 28 and 29 which, as explained later, are responsible for the particular drive selection of the module for additional handpieces. When, due to the actuation of a foot switch 15, the evaluation electronics 20 receives an on signal on a control line 30 which is connected to another input of the AND gate 27, a signal travels on a control line 31 and is applied to relay 32 to close a switch in line 58 to connect the output of the motor supply or power 26 to the line 57. In the present case, for example, the required operating voltage for the drive motor of 0 to 24 volts is created by the amount of depression of the switch 15 and travels through the line 57 to a line 44 and to sockets f and g wherein socket f is a "−" and socket g is a "+".

It should be noted that the same procedure will occur whether or not the instrument 3 is connected to the coupling member 8 or to the coupling members 9, 10 or 11. In each case, a different light barrier would supply a corresponding control signal and the control means 20 is associated with each of these particular coupling members.

If instead of connecting an electrical motor dental handpiece 3, a turbine handpiece 4 is connected, then the bridge elements A, B, D and E as schematically illustrated by combination 53 in FIG. 4a are utilized. As in the instance with the bridge connection 52, the pins A and B indicate that a handpiece has been connected and energize the light barrier for the recess of the holder 2. The elements D and E apply signals to various gates 33–36 wherein the gates 33 and 34 are OR gates, the gate 35 is an AND gate and the gate 36 is a NAND gate. In this arrangement, a signal is applied on the line 45 which is connected to a relay 47 and causes the switch to move from the illustrated position to a position causing an opening in the line 57. Thus, no electrical power is applied to the various sockets the f, g and h, and only operating agents such as drive air, spray air and spray water, which are required for operation of a turbine 4 are transferred through the channels 16 with the opening of the various solenoid valves 37. If desired, the operation of the valves 37 can be controlled by the foot switch 15 which would regulate the amount of power applied on line 51.

If an instrument 5, which is an ultrasonic-type instrument, is utilized, its coding pins will be interconnected or bridged as illustrated schematically by the combination 54 in FIG. 4a. As a result, the pins A, B and D are energized and apply signals to the evaluation means 20. As a result of the connection of the three pins A, B and D, when an ultrasonic dental handpiece has been removed from the associated recess, a signal is provided on line 45 and an output from the AND gate 23 creates a command signal on the line 39. As in the previous description, the line 45 causes the relay 47 of FIG. 3 to switch from the illustrated position to a position interconnecting an output of an ultrasonic supply module 41 to the line 44. A signal on the line 39 causes the relay 40 to close the switch to connect the ultrasonic module 41 to the power supply 26. In addition, a signal on the line 39 will cause the heating of the spray water normally associated with the other handpiece to be switched off. Thus, with actuation of the foot switch 15, power from the supply 26 passes through the ultrasonic module 41 and is connected to the sockets f and g. It should be noted that as in the previous embodiment, fluid would be applied to the channels 16; however, the connecting member for an ultrasonic handpiece may have dummy plugs for the plug 17 so that no flow of the various gases and water will occur.

In FIG. 4a, a connection arrangement is schematically illustrated as combination 55, which has pins A, B and E bridged or conncted together. This arrangement is used for a high frequency "HF" surgical handpiece. The surgical handpiece has an HF supply module 42. In the control means with the use of the pins A, B and E, and the removal of the HF handpiece from the recess 6, a control signal is applied on line 45 and the output of the AND gate 18 which is line 46. As in the previous embodiments, line 45 causes a relay 47 to switch the relay from the position illustrated to the opposite position and line 46 causes the relay 48 to move its switch from the illustrated position to connect the line 44 to the output of the HF module 42. In addition, a signal on the line 46 causes the relay 43 to close so that the HF module 42 is in the circuit for the power supply 26 which will be connected when actuation of the foot switch 15 occurs. Thus, a high frequency output is applied to the contacts f and g and the HF surgical supply module 42 is then connected to supply an operating voltage for the HF surgical handpiece through the contact pins such as F and G.

Depending on which connecting member for which handpiece is secured on the coupling member, various and different types of operating voltages are applied. For example, when the connecting member attached to an ultrasonic handpiece is connected as mentioned hereinabove, the relay 47 is switched from the illustrated position to a position connecting the output of the ultrasonic module 41 to the sockets f, g and h to supply the required ultrasonic transducer of the handpiece with the necessary operating voltage. As mentioned, when an electric motor-driven handpiece such as 3 is connected, then the power drive from the power source 26 is applied to the sockets to drive the electric motors and finally if a high frequency handpiece is attached, then the output of high frequency module 42 is connected. Finally, if a turbine-driven handpiece such as 4 is connected, no electrical power is applied to the sockets f, g and h.

Although various minor modifications may be suggested by those versed in the art, it should be understood that I wish to embody within the scope of the patent granted hereon, all such modifications as reasonably and properly come within the scope of my contribution to the art.

I claim:

1. In an apparatus for supporting a dental handpiece and for supplying necessary operating agents to the handpiece, said handpiece having a hose containing supply lines extending to a connecting member, said apparatus including a housing having support means including at least one support recess for receiving and storing a dental handpiece, a coupling member for each support means coacting with the connecting member of the handpiece to connect agent supply lines in the housing to the supply lines of the hose of the handpiece, and control means for controlling the flow of agents to the elements in the coupling member, the improvements comprising said housing including a source of water, a source of air and at least one source of electrical power, each coupling member being disposed in an easily accessible portion of the housing, said connecting and coupling members being designed for easy releasable interconnection, said coupling member being constructed with elements for separately transferring electrical power, air and water from the sources in the housing to the connecting member of the handpiece, said control means having evaluation means for receiving signals indicating the type of handpiece being connected to the coupling member and selectively connecting the various sources to the elements of the coupling member in response to the indicated type of handpiece, and said coupling member and connecting member having cooperating coding means for creating a signal to indicate the type of handpiece being connected by the coupling member so that the evaluation means automatically selects the desired agents for a specific type of handpiece when that handpiece is connected to the coupling member.

2. In an apparatus according to claim 1, wherein each of the support recesses is provided with means determining the presence of a handpiece in the recess and wherein the coding means activates the means for determining the presence of a handpiece in the recess when a connecting member of the handpiece is interconnected to the coupling member associated with the recess.

3. In an apparatus according to claim 2, wherein the coding means comprise pins disposed on one of the members received in sockets disposed in the other member, said member having the pins having the same number of pins with the particular coding determining by a bridge connection of selected pins.

4. In an apparatus according to claim 1, wherein each of the coupling members are rotatably mounted on the housing.

5. In an apparatus according to claim 1, wherein the apparatus includes at least two different types of electrical power sources and wherein the evaluation means selects the desired power source in response to the signal received.

6. In an apparatus according to claim 5, wherein the elements in one of the members comprise projecting tubular channels received in sockets for transferring fluid agents and projecting pins received in sockets for providing the coding means and for transferring electrical power.

* * * * *